United States Patent [19]

Collica et al.

[11] 3,984,695
[45] Oct. 5, 1976

[54] RADIATION GUARD APPARATUS

[75] Inventors: Carl Collica, New Rochelle; Leonard Epifano, Rye; Ralph Farella, Scarsdale, all of N.Y.

[73] Assignee: Medi-Ray, Inc., Tuckahoe, N.Y.

[22] Filed: Jan. 6, 1975

[21] Appl. No.: 538,968

[52] U.S. Cl. .............................. 250/515; 250/519
[51] Int. Cl.² ........................................... G21F 3/00
[58] Field of Search ........... 250/515, 517, 518, 519, 250/520

[56] References Cited
UNITED STATES PATENTS

| | | | |
|---|---|---|---|
| 2,003,752 | 6/1935 | Landt | 250/519 X |
| 2,720,105 | 10/1955 | Billups | 250/517 X |
| 3,030,508 | 4/1962 | Mort et al. | 250/515 X |

*Primary Examiner*—Archie R. Borchelt
*Attorney, Agent, or Firm*—Martin Novack

[57] ABSTRACT

Radiation shielding apparatus for use in conjunction with a pad on a table. The apparatus comprises a set of units, each unit comprising a pair of joined substantially flat orthogonal flaps. The flaps are formed of a radiation shielding material and are adapted for removable placement under the pad whereby one flap contacts the table and the other flap extends vertically from an edge thereof. In a preferred embodiment of the invention the set consists of five units that provide protection around three sides of a rectangular table. In this embodiment, two of the units are identical and have asymmetrical trapezoidal flaps, and two others of the units are also identical, but have trapezoidal flaps which are of reversed orientation with respect to the first-mentioned two units.

6 Claims, 4 Drawing Figures

RADIATION GUARD APPARATUS

BACKGROUND OF THE INVENTION

This invention relates to radiation shielding apparatus and, more particularly, to a radiation guard especially suitable for use in conjunction with a portable table.

Medical personnel should be protected from extended exposure to patients that have received radioactive materials for therapy, tracing, etc. Precautions, such as using leaded syringe shields, are normally taken when injecting radioactive materials into a patient, but during the subsequent moving and testing of the patient precautions are found inconvenient and are often dispensed with. While exposure to individual "radiating" patients may not prove harmful, the cumulative effect of numerous exposures can be dangerous to medical personnel.

SUMMARY OF THE INVENTION

The present invention is directed to a radiation guard apparatus comprising a set of radiation guard units that are especially suited for use in conjunction with a table having a pad, for example a portable table. In accordance with the invention, there are provided a plurality of units, each unit comprising a pair of joined substantially flat orthogonal flaps, the flaps being formed of a radiation shielding material. The flaps are adapted for removable placement under the pad whereby one flap contacts the table and the other flap extends vertically from an edge thereof.

In a preferred embodiment of the invention the plurality of units comprises five units proportioned to fit as a set around three sides of a rectangular table. In this embodiment, two of the units are identical and have asymmetrical trapezoidal flaps. Two others of the units are also identical, but have trapezoidal flaps which are of reversed orientation with respect to the first-mentioned two units.

Further features and advantages of the invention will become more readily apparent from the following detailed description when taken in conjunction with the accompanying drawings.

DESCRIPTION OF THE PREFERRED EMBODIMENT

Figure 1:
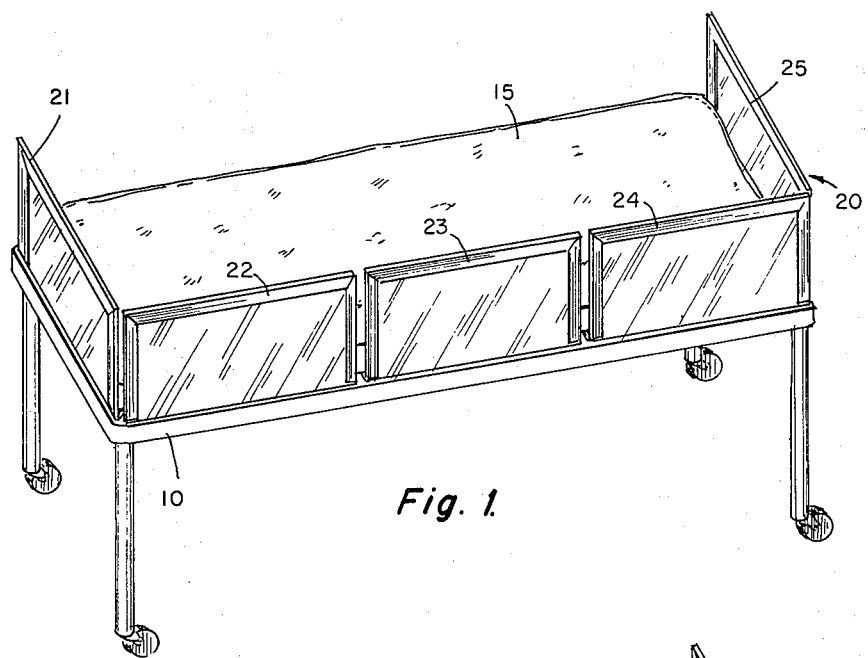
FIG. 1 illustrates an embodiment of the invented radiation guard apparatus being used in conjunction with a portable table and pad.
Figure 2:
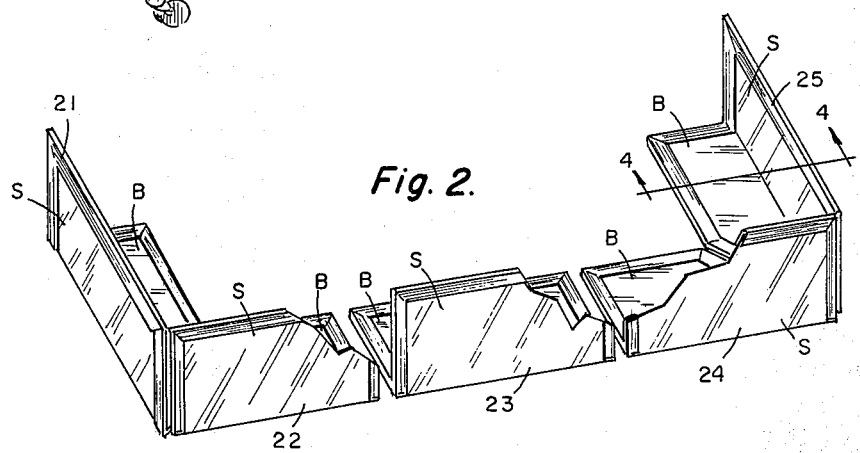
FIG. 2 is perspective view of the units of the guard apparatus arranged as in FIG. 1, but without the table and pad for illustrative clarity.

Referring to FIG. 1, there is shown a portable table 10 having a pad or mattress 15 thereon, and a radiation guard apparatus 20 in accordance with the invention, the apparatus 20 comprising a set of guard units designated by reference numerals 21, 22, 23, 24 and 25. The guard units, which can be seen in perspective in FIG. 2, are each seen to be formed of a pair of substantially flat orthogonal flaps; i.e., a "side" flap, S, and a "bottom" flap, B. In the illustration of FIG. 1, the bottom flaps are not visible, having been inserted under the pad 15 and retained between the surface of table 10 and the pad 15.

Figure 3:
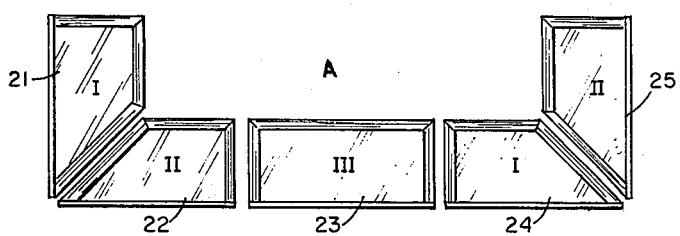
FIG. 3 is a plan view of the bottom flaps of the guard units arranged as in FIGS. 1 and 2.

FIG. 3 shows a plan view of the bottom flaps of the guard units when arranged as in FIGS. 1 and 2. The bottom flap of unit 23, labeled as III, is rectangular. The units 21 and 24, which are identical, are asymmetrical trapezoids, labeled I. The units 22 and 25, labeled II, are also identical asymmetrical trapezoids, but are of reversed orientation with respect to the units I. Therefore, only three basic shapes are seen to be necessary for the protective arrangement illustrated.

Figure 4:
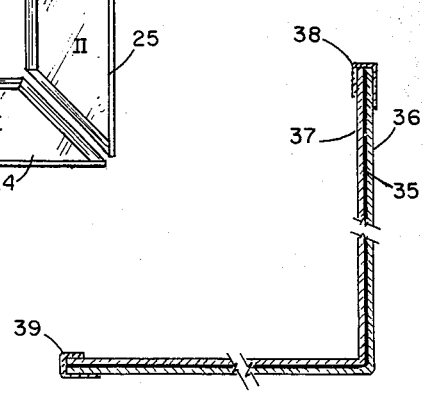
FIG. 4 is a cross-sectional view of a guard unit as taken through a section indicated by arrows 4—4 of FIG. 2.

FIG. 4 shows the construction of the individual guard units in accordance with the present embodiment. A central lead sheet 35, typically 1/32 inch thick, is sandwiched between supportive aluminum sheets 36 and 37, typically each 1/16 inch thick. Edge brackets 38 and 39, which may be aluminum extrusions, are also provided.

In operation, the guard units can be easily inserted around the table after a patient has been placed thereon. In addition to the protection provided by the side flaps, the bottom flaps serve to protect the legs and lower trunk of medical personnel by absorbing radiation that might normally pass at an angle through a transmissive table. During a transmission scan procedure, the unshielded area A (FIG. 3) allows various types of scans to be performed with the units in place. Also, if desired, less than the full set can be used to provide shielding around a particular local body area. When not in use, the similar shapes of the individual units allow them to be readily "nested" for convenient compact storage.

The invention has been described with reference to a particular embodiment but variations within the spirit and scope of the invention will occur to those skilled in the art. For example, it will be understood that the terms "table" and "mattress" or "pad" are used generically and not in a limiting sense. Also, it will be recognized that alternative materials could be used to construct the guard units.

We claim:

1. Radiation shielding apparatus for use in conjunction with a pad on a table, said apparatus comprising a plurality of units, each unit comprising a pair of joined substantially flat orthogonal flaps, said flaps being formed of a radiation shielding material and adapted for removable placement under said pad, whereby one flap contacts said table and the other flap extends vertically from an edge thereof.

2. Apparatus as defined by claim 1 wherein each of said flaps comprises a sheet of high density shielding material affixed to a supportive sheet of rigid material.

3. Apparatus as defined by claim 1 wherein said plurality of units comprises five units proportioned to fit as a set around three sides of a rectangular table.

4. Apparatus as defined by claim 3 wherein two of said units are identical and each has an asymmetrical trapezoidal flap, and two others of said units are also identical but each of said two others has a trapezoidal flap which is of reversed orientation with respect to the trapezoidal flap of each of the first-mentioned two units.

5. Apparatus as defined by claim 4 wherein the last of said units is rectangularly shaped.

6. Apparatus as defined by claim 4 wherein each of said flaps comprises a sheet of high density shielding material affixed to a supportive sheet of rigid material.

* * * * *